US009040028B2

(12) United States Patent
Breakspear et al.

(10) Patent No.: US 9,040,028 B2
(45) Date of Patent: May 26, 2015

(54) HAIR COSMETIC COMPOSITION

(75) Inventors: Steven Breakspear, Sumida-ku (JP); Takashi Ito, Sumida-ku (JP); Kenzo Koike, Sumida-ku (JP); Artur Cavaco-Paulo, Guimaraes (PT)

(73) Assignee: KAO CORPORATION, Tokyo (JP)

( * ) Notice: Subject to any disclaimer, the term of this patent is extended or adjusted under 35 U.S.C. 154(b) by 352 days.

(21) Appl. No.: 12/680,013

(22) PCT Filed: Sep. 26, 2008

(86) PCT No.: PCT/JP2008/068008
§ 371 (c)(1),
(2), (4) Date: Jun. 28, 2010

(87) PCT Pub. No.: WO2009/041739
PCT Pub. Date: Apr. 2, 2009

(65) Prior Publication Data
US 2010/0272666 A1    Oct. 28, 2010

(30) Foreign Application Priority Data

Sep. 28, 2007 (JP) ................................ 2007-253291

(51) Int. Cl.
*A61K 8/64* (2006.01)
*A61K 38/16* (2006.01)
*A61Q 5/02* (2006.01)
*A61Q 5/06* (2006.01)
*A61Q 5/08* (2006.01)
*A61Q 5/12* (2006.01)
*A61K 8/34* (2006.01)
*A61K 8/37* (2006.01)
*A61K 8/49* (2006.01)

(52) U.S. Cl.
CPC . *A61K 8/64* (2013.01); *A61K 8/347* (2013.01); *A61K 8/37* (2013.01); *A61K 8/4913* (2013.01); *A61Q 5/02* (2013.01); *A61Q 5/06* (2013.01); *A61Q 5/08* (2013.01); *A61Q 5/12* (2013.01)

(58) Field of Classification Search
CPC ........... A61K 8/64; A61K 38/16; A61Q 5/02; A61Q 5/06; A61Q 5/08; A61Q 5/12
USPC ........................................................ 424/70.1
See application file for complete search history.

(56) References Cited

U.S. PATENT DOCUMENTS

| | | | |
|---|---|---|---|
| 3,904,748 A | | 9/1975 | Eckert et al. |
| 7,273,847 B2 * | | 9/2007 | McCormack, Jr. ............. 514/2.3 |
| 2002/0058017 A1 * | | 5/2002 | Tajima et al. ................. 424/70.1 |
| 2004/0156810 A1 * | | 8/2004 | Tachizawa et al. ......... 424/70.12 |

FOREIGN PATENT DOCUMENTS

| | | |
|---|---|---|
| CN | 1863501 A | 11/2006 |
| DE | 2 151 740 | 4/1973 |
| EP | 0 129 801 A2 | 1/1985 |
| EP | 0 129 801 A3 | 1/1985 |
| EP | 1 570 832 A1 | 9/2005 |
| JP | 60-4114 A | 1/1985 |
| JP | 61-7211 A | 1/1986 |
| JP | 5-43424 A | 2/1993 |
| JP | 9-110647 A | 4/1997 |
| JP | 11-302300 | 11/1999 |
| JP | 2000-86462 | 3/2000 |
| JP | 2004-269430 | 9/2004 |
| JP | 2005-272400 A | 10/2005 |
| JP | 2006-508919 A | 3/2006 |
| JP | 2006-131579 | 5/2006 |
| JP | 2007-1953 | 1/2007 |
| JP | 2007-137835 A | 6/2007 |
| WO | WO 2004/024176 A1 | 3/2004 |
| WO | WO 2004/048399 A2 | 6/2004 |
| WO | WO 2004/048399 A3 | 6/2004 |
| WO | WO 2005/025505 A2 | 3/2005 |
| WO | WO 2006/028503 A1 | 3/2006 |
| WO | WO 2007/136286 * 11/2007 ............... A61K 8/64 |

OTHER PUBLICATIONS

Definition of derivative from http://cancerweb.ncl.ac.uk/omd/about. html, pp. 1-5. Accessed Jul. 7, 2005.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Benzyl Alcohol is naturally occurring from www.parachem.com/news-articles/Parchem-Leading-Supplier-of-Natural-Benzyl-Alcohol, pp. 1-3. Accessed Aug. 19, 2014.*

(Continued)

*Primary Examiner* — Julie Ha
(74) *Attorney, Agent, or Firm* — Oblon, McClelland, Maier & Neustadt, L.L.P.

(57) ABSTRACT

The present invention provides a hair cosmetic composition containing the following components (a) and (b) and a hair treatment method in which the hair cosmetic composition is applied to the hair: (a) one or two or more peptides each having the number of amino acid residues being 5 to 50, and having neither a sulfur-containing amino acid residue nor a derivative thereof; and (b) a hair-swelling organic solvent.

7 Claims, No Drawings

(56) References Cited

OTHER PUBLICATIONS

Database WPI Week 200715, Thomson Scientific, XP-002529684, 2007, 2007-145594, 4 pages.
Clarence R Robbins, "Chemical and Physical Behaviour of Human Hair", Chapter 8, Springer-Verlag, 2002, 46 pages.
Chinese Office Action issued May 25, 2011, in Patent Application No. 200880107116.8 (with English-language translation).
Office Action issued Feb. 5, 2013 in Japanese Patent Application No. 2007-253291 with English language translation.
Shin Keshouhin Handbook (New Handbook of Cosmetics), Nikko Chemical Co., Ltd. et al., (9. Hair Conditioner) Oct. 30, 2006, pp. 578-582 with cover page and English language translation.
Office Action issued Feb. 16, 2013 in Chinese Patent Application No. 200880107116.8 (with English translation).
B.H. Scortichini, et al., "Teratologic evaluation of 2-phenoxyethanol in New Zealand white rabbits following dermal exposure", Fundamental and Applied Toxicology, vol. 8, Dec. 31, 1987, pp. 272-279.
William E. Morton, "Occupational phenoxyethanol neurotoxicity: A report of three cases", Journal of Occupational Medicine, vol. 32, No. 1, Jan. 31, 1990, pp. 42-45.
Communication of a notice of opposition issued Aug. 17, 2012 in European Application No. 08833671.4 (With English Translation).
E. W. Flick, "Cosmetic and Toiletry Formulations", Second edition, vol. 7, 1999, pp. 154-155.
"Hexapeptide-2", Cosmetics—CosIng [Cosmetics Directive (v.1)]. Aug. 9, 2012, 1 page.

* cited by examiner

```
SEQUENCE LISTING

<160> NUMBER OF SEQ ID NOS: 4

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide (1)

<400> SEQUENCE: 1

Ala Thr Leu His Asp Phe Arg His Gln Ile Leu Gln Thr Arg Gly Ala
1               5                   10                  15

Leu Ser Leu Gln Gly Lys
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide (2)

<400> SEQUENCE: 2

Ala Ala Ala Ala Lys Ala Ala Ala Lys Ala Ala Ala Ala Lys Ala
1               5                   10                  15

Ala Ala Ala Lys
            20

<210> SEQ ID NO 3
<211> LENGTH: 22
<212> TYPE: PRT
<213> ORGANISM: Artificial Sequence
```

```
-continued

<220> FEATURE:
<223> OTHER INFORMATION: Description of Artificial Sequence: Synthetic
      peptide (3)

<400> SEQUENCE: 3

Gln Gly Gln Val Gln His Leu Gln Ala Ala Phe Ser Gln Tyr Lys Lys
1               5                   10                  15

Val Glu Leu Phe Pro Lys
            20

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide (4)

<400> SEQUENCE: 4

Phe Pro Ile Pro Leu Pro Tyr Cys Trp Leu Cys Arg Ala Leu Ile Lys
1               5                   10                  15

Arg Ile Gln Ala Met Ile Pro Lys Gly Lys
            20                  25
```

HAIR COSMETIC COMPOSITION

FIELD OF THE INVENTION

The present invention relates to a hair cosmetic composition capable of repairing the hair damaged by various external factors.

BACKGROUND OF THE INVENTION

Hair undergoes physical and chemical denaturalization of keratin proteins caused by various external factors and undergoes phenomena such as the generation of split ends or broken hair, the increase of frictional force of hair surface, the degradation of hair resilience and toughness, the mutual tangling of hair strands, hair dryness and the degradation of the feeling of the hair to the touch (see, Non-Patent Document 1).

For the purpose of preventing or overcoming such hair damage as described above, silicones, polysaccharides, polypeptides, polypeptide derivatives, surfactants, polyols, amino acids, fats and oils, plant extracts, ultraviolet absorbers or ultraviolet scatterers, and the like are used singly or as a combination of two or more thereof; among them, polypeptides or polypeptide derivatives attract attention from the viewpoints of affinity to the hair and effectiveness for the hair; accordingly a large number of technical proposals have been made.

For example, Patent Document 1 has proposed the use of a protein most abundantly containing amino acids having hydroxyl groups; Patent Document 2 has proposed the use of γ-polyglutamic acid; Patent Document 3 has proposed the use of an acylated peptide obtained by condensation reaction between a peptide obtained by hydrolyzing a protein and a lanolin fatty acid having a specific composition; and Patent Document 4 has proposed the use of a peptide in which side chain amino groups thereof are silylated.

The amino acid composition of each of these polypeptides or polypeptide derivatives is a mixture having a broad molecular weight distribution, however, or has an amino acid composition which is not necessarily constant, in such a way that the composition varies from one protein source to another protein source or from one production unit to another production unit; accordingly, the above-described effects tend to be varied. In addition, polypeptides or polypeptide derivatives having a large molecular weight are generally low in penetrability into hair, and modify the hair surface to effect only sensory improvements, involving properties such as appearance and feeling to the touch, and offer insufficient effects for substantively preventing or improving hair damage in the sense that the internal condition of the hair is improved. On the other hand, polypeptides or polypeptide derivatives having a small molecular weight have a low ability to remain on the hair, and accordingly have low persistence of the effect of the prevention or improvement of hair damage. Thus, in both cases, there have been problems that it is impossible to sufficiently prevent the generation of split ends or broken hair.

[Non-Patent Document 1] C. R. Robbins, "Chemical and Physical Behavior of Human Hair," Chapter 8, Springer-Verlag, New York, 2002
[Patent Document 1] JP-A-2006-131579
[Patent Document 2] JP-A-2004-269430
[Patent Document 3] JP-A-11-302300
[Patent Document 4] JP-A-2000-086462

SUMMARY OF THE INVENTION

The present invention provides a hair cosmetic composition containing the following components (a) and (b):

(a) one or two or more peptides each having the number of amino acid residues between 5 and 50, and having neither a sulfur-containing amino acid residue nor a derivative thereof; and
(b) a hair-swelling organic solvent.

Further, the present invention provides a hair treatment method in which the above-described hair cosmetic composition is applied to the hair.

DETAILED DESCRIPTION OF THE INVENTION

The present invention relates to a hair cosmetic composition capable of repairing the hair damaged by various external factors and a method for repairing the hair by using the hair cosmetic composition.

The present inventors discovered that some specific peptides are satisfactory in penetrability into hair and the use of such peptides in a hair cosmetic composition, together with an organic solvent to swell the hair, attains a remarkable damage repairing effect.

[Component (a)]

Each of the peptides as component (a) used in the hair cosmetic composition contains neither a sulfur-containing amino acid residue nor a derivative thereof which forms an intramolecular crosslinkage or an intermolecular crosslinkage; hence, such a peptide has such small interaction with hair proteins that it exhibits penetrability into hair.

From the viewpoint of the higher penetrability into hair, in the peptides of component (a), the number of the basic amino acid residues and the number of the nonpolar amino acid residues are 5 to 25% and 30 to 85%, respectively, of the total number of the amino acid residues in the whole sequence.

Here, as the nonpolar amino acids and the basic amino acids, any compounds known as nonpolar amino acids and basic amino acids may be adopted, respectively. Examples of the nonpolar amino acids include glycine, alanine, leucine, isoleucine, phenylalanine, proline, tryptophan and valine. Examples of the basic amino acids include arginine, histidine and lysine. Additionally, examples of polar amino acids include asparagine, glutamine, serine, threonine and tyrosine, and examples of acidic amino acids include asparagic acid and glutamic acid.

Additionally, from the viewpoints of the blendability in the composition and the stability in the composition, the peptide as component (a) has the number of amino acid residues being preferably 10 to 30 and more preferably 20 to 25, and the molecular weight being preferably 1500 to 3500 and more preferably 2000 to 2800. Preferable among others is the peptide having a number of basic amino acid residues being 4 or 5 and the number of nonpolar amino acid residues being 10 or more. Further, as component (a), preferred is the peptide in which the C-terminated amino acid is a basic amino acid, and more preferable is the peptide in which the C-terminated amino acid is lysine.

Specific examples of the peptides preferable as component (a) include a peptide represented by any of Sequence Nos. 1 to 3, a peptide having an amino acid sequence derived from the aforementioned peptide by deleting therefrom, substituting therein or adding thereto one or a few amino acids and having penetrability into hair, and a peptide composed of an amino acid sequence having 80% or above, more preferably 90% or above, and even more preferably 95% or above, homology to the aforementioned peptide and having penetrability into hair.

In the present invention, the amino acid sequence homology is calculated by means of the Lipman-Pearson method (Science, 227, 1435 (1985)). Specifically, the amino acid sequence homology is calculated by using the homology analysis (Search homology) program in the genetic information processing software Genetyx-Win (product of Software Development Co., Ltd.) and by setting the parameter, Unit size to compare (ktup), at 2.

The component (a) can be used singly or as a combination of two or more thereof, and the content of the component (a) in the hair cosmetic composition of the present invention is preferably 0.001 to 5% by mass, more preferably 0.005 to 3% by mass and even more preferably 0.01 to 2.5% by mass.

[Component (b)]

The component (b) used in the present invention is not particularly limited and may be any liquid organic compound as long as the compound swells the hair. Examples of such compounds may include lower alkylene carbonates, aromatic alcohols and N-alkylpyrrolidones.

More specifically, examples of the lower alkylene carbonates include ethylene carbonate and propylene carbonate. Examples of the aromatic alcohols include benzyl alcohol, benzyloxyethanol, β-phenylethyl alcohol, cinnamyl alcohol, phenyl propanol, α-methylbenzyl alcohol, dimethyl benzyl carbinol, phenoxyethanol and p-anisyl alcohol. Examples of the N-alkylpyrrolidones include N-methylpyrrolidone, N-ethylpyrrolidone and N-octylpyrrolidone.

Preferable among these hair-swelling organic solvents are propylene carbonate, benzyl alcohol and benzyloxyethanol, from the viewpoints of enhancement of the effects of component (a), and the feeling in use, viscosity and compatibility with various other base materials of the composition.

The component (b) can be used singly or as a combination of two or more thereof, and the content of the component (b) in the hair cosmetic composition of the present invention is preferably 0.1 to 20% by mass, more preferably 0.25 to 15% by mass and even more preferably 0.4 to 10% by mass.

[Other Components]

Furthermore, the hair cosmetic composition of the present invention may contain a surfactant. As the surfactant, any of a cationic surfactant, a nonionic surfactant, an amphoteric surfactant and an anionic surfactant can be used.

Preferable as the cationic surfactant are long chain monoalkyl quaternary ammonium salts. Specific examples of such quaternary ammonium salts include cetrimonium chloride, steartrimonium chloride, behentrimonium chloride, stearalconium chloride and benzalconium chloride; preferable among these are steartrimonium chloride and behentrimonium chloride.

Examples of the type of the nonionic surfactant include polyoxyalkylene alkyl ether, polyoxyalkylene alkenyl ether, higher fatty acid sucrose ester, polyglycerin fatty acid ester, higher fatty acid mono- or diethanol amide, polyoxyethylene hydrogenated castor oil, polyoxyethylene sorbitan fatty acid ester, polyoxyethylene sorbit fatty acid ester, alkyl saccharide, alkyl amine oxide and alkylamide amine oxide. Among these, polyoxyalkylene alkyl ether and polyoxyethylene hydrogenated castor oil are preferable, and polyoxyethylene alkyl(12 to 14) ether is more preferable.

Examples of the type of the amphoteric surfactant include imidazoline, carbobetaine, amidobetaine, sulfobetaine, hydroxysulfobetaine and amidosulfobetaine.

Example of the type of the anionic surfactant include alkylbenzenesulfonic acid salt, alkyl or alkenyl ether sulfuric acid salt, alkyl or alkenyl sulfuric acid salt, olefin sulfonic acid salt, alkane sulfonic acid salt, saturated or unsaturated fatty acid salt, alkyl or alkenyl ether carboxylic acid salt, α-sulfonic fatty acid salt, N-acylamino acid, phosphoric acid mono- or diester and sulfosuccinic acid ester. Examples of the alkyl ether sulfuric acid salt include polyoxyethylene alkyl ether sulfuric acid salt. Examples of the counter ions of the anionic groups in these anionic surfactants include: alkali metal ions such as sodium ion and potassium ion; alkali earth metal ions such as calcium ion and magnesium ion; ammonium ion; and alkanol amines (for example, monoethanolamine, diethanolamine and triethanolamine, and triisopropanolamine) having one to three alkanol groups containing two or three carbon atoms.

The surfactant can be used singly or as a combination of two or more thereof, and the content of the surfactant in the hair cosmetic composition of the present invention is 0.1 to 30% by mass and additionally preferably 0.5 to 20% by mass from the viewpoints of the feeling to the touch and the emulsification performance.

Furthermore, the hair cosmetic composition of the present invention may contain a cationic polymer. The cationic polymer means a polymer having a cationic group or a group capable of being ionized to a cationic group, and includes such an amphoteric polymer that is cationic as a whole. Specifically, examples of the cationic polymer include a water-soluble polymer having an amino group or an ammonium group in the side chain of the polymer chain or containing a diallyl quaternary ammonium salt as a constitutional unit, such as cationized cellulose derivatives, cationic starch, cationized guar gum derivatives, polymers or copolymers of dially quaternary ammonium salt and quaternarized polyvinyl pyrrolidone derivatives. From the viewpoints of the soft feeling, smooth feeling and easy finger-combing at the time of shampooing, easy manageability and moisture retention of the hair at the time of dryness, and the stability of the formulation, preferable among these are polymers containing as the constitutional unit dially quaternary ammonium salt, quaternarized polyvinyl pyrrolidone derivatives and cationized cellulose derivatives, and more preferable are a copolymer or a polymer of diallyl quaternary ammonium salt and cationized cellulose derivatives.

Specific examples of the cationic polymers include: dimethyldiallylammonium chloride polymer (polyquaternium-6, for example, Merquat 100, product of Nalco Japan Co., Ltd.); dimethyldiallylammonium chloride/acrylic acid copolymer (polyquaternium-22, for example, Merquat 280 and ditto 295, products of Nalco Japan Co., Ltd.); dimethyldiallylammonium chloride/acrylic acid amide copolymer (polyquaternium-7, for example, Merquat 2200, product of Nalco Japan Co., Ltd.); quaternarized polyvinyl pyrrolidone derivatives (polyquaternium-11, for example, Gafquat 734, ditto 755 and ditto 755N, products of ISP Japan Ltd.); cationized cellulose derivatives (polyquaternium-10, for example, Poiz C-150L, ditto C-60H and ditto C-80M, products of Kao Corp.; UCARE polymer JR-125, ditto JR-400, ditto JR-30M, ditto LR-400 and ditto LR-30M, products of Dow Chemical Japan Ltd.).

These cationic polymers can be used singly or as a combination of two or more thereof; from the viewpoints of the improvement of the feeling to the touch and the formulation stability, the content of the cationic polymer(s) in the hair cosmetic composition of the present invention is preferably 0.001 to 20% by mass, more preferably 0.01 to 10% by mass and even more preferably 0.05 to 5% by mass.

The hair cosmetic composition of the present invention may contain silicones for the purpose of imparting excellent feeling upon use. Examples of the silicones include: polysiloxanes; modified silicones (for example, amino-modified silicone, fluorine-modified silicone, alcohol-modified silicone, polyether-modified silicone, epoxy-modified silicone and alkyl-modified silicone); and cyclic polysiloxane; preferable among these are polysiloxanes, polyether-modified silicone and amino-modified silicone. Specific commercially available examples of the silicones include: polysiloxanes such as SH200-1,000,000 cs, BY11-026, FZ-2231 (products of Dow Corning Toray Co., Ltd.) and TSF451-100MA (product of Momentive Performance Materials Japan LLC); polyether-modified silicones such as TSF4440 (product of Momentive Performance Materials Japan LLC), KF-6005, KF-6012 (products of Shin-Etsu Chemical Co., Ltd.) and SS-2910 (product of Dow Corning Toray Co., Ltd.); amino-modified silicones such as XF42-B8922, XF42-C0330 (products of Momentive Performance Materials Japan LLC), SF8451C, SF8452C, SF8457C, SM8704C (products of Dow Corning Toray Co., Ltd.) and KF-867 (product of Shin-Etsu Chemical Co., Ltd.); and mixtures of amino-modified silicones with polysiloxanes such as KF-1046 (product of Shin-Etsu Chemical Co., Ltd.).

The above-described silicones can be used singly or as a combination of two or more thereof; from the viewpoints of the attainment of sufficient advantageous effects and the suppression of feeling of stickiness, the content of the silicone(s) in the hair cosmetic composition of the present invention is preferably 0.02 to 40% by mass, more preferably 0.1 to 20% by mass and even more preferably 0.2 to 15% by mass.

The hair cosmetic composition of the present invention may contain a higher alcohol from the viewpoints of the improvement of the feeling to the touch and stability. Such a higher alcohol forms a structure with the surfactant so as to prevent the segregation of the hair cosmetic composition and offers an advantageous effect to improve the feeling to the touch at the time of rinsing.

The higher alcohol is an alcohol having 8 to 26 carbon atoms, and preferably an alcohol having 16 to 22 carbon atoms; specific examples of such a higher alcohol include cetanol, stearyl alcohol and behenyl alcohol.

The higher alcohols can be used singly or as a combination of two or more thereof; the content of the higher alcohol(s) in the hair cosmetic composition of the present invention is 0.01 to 20% by mass and additionally preferably 0.1 to 10% by mass.

In the hair cosmetic composition of the present invention, water and, according to need, organic solvent(s) other than the component (b) are used as media. Examples of such organic solvents include: lower alkanols such as ethanol and 2-propanopl; polyols such as propylene glycol, 1,3-butanediol, diethylene glycol and glycerin; cellosolves such as ethyl cellosolve and butyl cellosolve; and carbitols such as ethyl carbitol and butyl carbitol.

To the hair cosmetic composition of the present invention, in addition to the above-described components, other components usually used as cosmetic raw materials can be added. Examples of such optional components include hydrocarbons, animal and plant fats and oils, higher fatty acids, natural and synthetic polymer ethers, a preservative, a chelating agent, a stabilizer, an antioxidant, a plant extract, an herbal medicine extract, vitamins, a fragrance ingredient and an ultraviolet absorber.

The hair cosmetic composition of the present invention can be prepared in any form as long as the form is applicable to hair; specific examples of such forms include a hair shampoo, a hair rinse, a hair conditioner, a hair dressing and a hair dye; and the hair cosmetic composition can be prepared in various formulation forms such as liquid, cream, gel, mist, foam and spray.

A hair treatment method using the hair cosmetic composition of the present invention is such that according to the application purpose of the hair cosmetic composition, the hair cosmetic composition is applied to dried or moisturized hair in a mass ratio (hair cosmetic composition/hair) of 0.01 to 3, and allowed to stand for a predetermined period of time and has only to be washed away. The standing time elapsed from the time of the application to hair is preferably 1 minute to 24 hours; when allowed to stand for more preferably 1 minute to 10 minutes in application as hair shampoo, hair rinse or hair conditioner, for 30 minutes to 18 hours in application as hair dressing, and for 5 to 40 minutes in application as hair dye, from the viewpoint of the penetration into hair to a sufficient extent so as to enhance the advantageous effects of the present invention.

The following examples further describe and demonstrate embodiments of the present invention. The examples are given solely for the purpose of illustration and are not to be construed as limitations of the present invention.

EXAMPLES

In the below-described Examples and Comparative Examples, the peptides (belonging to the component (a)) shown in Sequence Nos. 1 to 3 are denoted by Peptide (1), Peptide (2) and Peptide (3), respectively. Additionally, the peptide (not belonging to the component (a)) shown in Sequence No. 4 is denoted by Peptide (4).

Example 1 and Comparative Examples 1 to 3

Test 1

The hair cosmetic composition of each composition shown in Table 1 was prepared according to a manner known per se in the art; test tresses prepared from Japanese female hair were treated according to the below-described method, and thereafter subjected to a fatigue-life test.

TABLE 1

| Component (% by mass) | Example 1 | Comparative Example 1 | Comparative Example 2 | Comparative Example 3 |
|---|---|---|---|---|
| Ethanol | 10.0 | 10.0 | 10.0 | 10.0 |
| Benzyl alcohol | 0.5 | 0.5 | — | 0.5 |
| Propylene glycol | 1.5 | 1.5 | 2.0 | 1.5 |
| Peptide (1) | 0.02 | — | 0.02 | — |
| Peptide (4) | — | — | — | 0.02 |
| Purified water | Balance | Balance | Balance | Balance |

[Test Tresses]

From a Japanese woman, about 100 straight hairs of 12 to 15 cm in length, not having been subjected to a hair dyeing treatment, a hair bleaching treatment nor a permanent treatment were obtained, and the entire length of the obtained hairs were subjected to eight times repetition of the bleaching cycle of the following four steps of:

(1) bleaching treatment with an equal amount of a commercially available bleach;

(2) washing with an equal amount of a commercially available shampoo;

(3) treatment with an equal amount of a commercially available hair conditioner; and (4) blow-drying.

The diameter in the vicinity of the midway point of each of the hairs was measured with a micrometer, and four sets of 15 hairs of 75 to 85 μm in diameter were selected. In each set of 15 hairs, the root ends of the hairs were fixed with an epoxy adhesive and an adhesive tape, and the tips of the hairs were trimmed so as for the length of the hairs to be 10 cm. Thus, four sets of test tresses were obtained.

[Treatment Method]

Treatment Step:

The hair cosmetic composition of each of Example 1 and Comparative Examples 1 to 3 was measured out in an amount of 5 mL and poured in a glass tube of 12 cm in total length, containing the entire of the test tress composed of 15 hairs. The test tress was wholly wetted with the hair cosmetic composition. The glass tube was immersed in a water bath maintained at 37° C. for 300 minutes while shaking at a rate of 100 times/min.

Washing and Drying Steps:

The test tress in the glass tube was taken out, transferred into a 30 mL total volume sample tube filled with ion-exchanged water, and twice subjected to 30-second vigorous shaking for washing. The test tress was placed on a plastic film in a stretched manner, a small amount of a commercially available shampoo was dropwise applied to the test tress, the plastic film was rolled up in a cylindrical shape in the direction of the extension of the test tress, and the test tress was washed with the shampoo by lightly rubbing the plastic film roll with fingertips for 1 minute. Then, the test tress was separated away from the plastic film, twice subjected to the above-described washing operation using the sample tube, and thereafter dried overnight naturally in a suspended manner.

[Fatigue-Life Test]

Each of the test tresses was cut at a root position thereof to be separated into 15 hairs, and on both ends of each of the hairs, round crimping terminals were equipped and the tresses were fixed with an epoxy adhesive to the round crimping terminals so as for the total length of the hair to be 8 cm. Each of the hairs was allowed to stand overnight in a test chamber controlled at 20° C. and a relative humidity of 65%, in a manner suspended with the root end as the upper end.

In a fatigue-life measurement apparatus (Journal of Cosmetic Science, Vol. 50, pp. 198 to 200, (1999)) installed in a test room, each of the hairs was set so as for the root end to be the upper end, and loaded with a weight of 55 g. The initial condition was set in such a way that each of the hairs was controlled to take a natural length free from the sensation of the weight by vertically moving the root end crimping terminal. A constant speed cyclic stretching was conducted in which the root end crimping terminal of every hair set in the apparatus was upwardly moved by 3 cm and got back to the initial condition with a period of 1 second, and the number of the cycles at which the hair was spontaneously broken due to fatigue was measured.

On the basis of the data thus obtained, the characteristic life ($\theta$) was derived in the following manner.

For the purpose of statistically dealing with the fatigue failure behavior, the "Weibull distribution" was used, which permits evaluating the variation characteristics over a broad range. From the Weibull distribution formula, the mathematical formula 2 is obtained by deriving twice the logarithms of both sides of the mathematical formula 1; and from the mathematical formula 2 thus derived, the parameter $\theta$ (characteristic life) is obtained. The x axis represents ln x and the y axis represents ln [ln [1/[1−F(x)]]], the individual data are plotted and an approximate straight line is obtained; from the intercept=$b\ln\theta$ and the slope=b, the characteristic life $\theta$ is derived (mathematical formula 3).

$$F(x) = 1 - \exp\left\{-\left(\frac{x}{\theta}\right)^b\right\}$$ [Mathematical formula 1]

$$\ln\left\{\ln\left(\frac{1}{1-F(x)}\right)\right\} = b\ln x - b\ln\theta$$ [Mathematical formula 2]

$$\theta = \exp\left(-\frac{\text{intercept}}{\text{slope}}\right)$$ [Mathematical formula 3]

In these formulas:

x: number of the cycles of breakage; F(x): Sequence number of breakage/Number of samples b: shape parameter $\theta$: characteristic life (the number of the cycles of the breakage of 63.2% of the number of the samples)

The characteristic lives obtained for the test tresses respectively treated with the hair cosmetic compositions of Example 1 and Comparative Examples 1 to 3 are shown in Table 2.

TABLE 2

| | Example 1 | Comparative Example 1 | Comparative Example 2 | Comparative Example 3 |
|---|---|---|---|---|
| Characteristic life ($\theta$)/$10^4$ | 6.3 | 3.0 | 3.1 | 3.1 |

Test 1 provided the results that the hairs treated with the hair cosmetic composition of the present invention were longer in characteristic life, and hence the hair cosmetic composition of the present invention is excellent in the effect of preventing the hair damage.

Test 2

The test tresses prepared from the hairs obtained from a Japanese woman, different in the number of bleaching treatment cycles, were treated by using the hair cosmetic composition of Example 1 shown in Table 1 by means of the following treatment method, and thereafter, evaluated on the basis of the fatigue-life test.

[Test Tresses]

From a Japanese woman, about 100 straight hairs of 12 to 15 cm in length, not having been subjected to a hair dyeing treatment, a hair bleaching treatment nor a permanent treatment were obtained, and were divided into two masses of approximately 50 hairs/equal amount. Each of the two masses of hairs was respectively subjected to two and eight times repetition of the bleaching cycle of the following four steps of:

(1) bleaching treatment with an equal amount of a commercially available bleach;

(2) washing with an equal amount of a commercially available shampoo;

(3) treatment with an equal amount of a commercially available hair conditioner; and (4) blow-drying.

The diameter in the vicinity of the midway point of each of the hairs was measured with a micrometer, and two sets of 15 hairs of 80 to 90 μm in diameter were selected from each of the bleaching-treated samples. In each set of 15 hairs, the root ends of the hairs were fixed with an adhesive and an adhesive tape, and the tips of the hairs were trimmed so as for the length of the hairs to be 10 cm. Thus, four sets of test tresses were obtained (two sets of twice treated tresses, and two sets of eight times treated tresses).

[Treatment Method]

For each of the test tresses, the hair cosmetic composition of Example 1 was measured out in an amount of 5 mL and poured in a glass tube of 12 cm in total length, containing the entire of the test tress composed of 15 hairs. The test tress was wholly wetted with the hair cosmetic composition. The glass tube was immersed in a water bath maintained at 37° C. for 60 minutes or 300 minutes while shaking at a rate of 100 times/min.

Then, the test tress was washed in the same manner as in Example 1, and dried overnight naturally in a suspended manner.

[Fatigue-Life Test]

The characteristic life (θ) of each of the test tresses was derived in exactly the same manner as in Test 1. The results thus obtained are shown in Table 3.

TABLE 3

|  | Test tress | | | |
|---|---|---|---|---|
|  | Tress treated with two bleaching cycles | | Tress treated with eight bleaching cycles | |
| Test treatment time/min | 60 | 300 | 60 | 300 |
| Characteristic life (θ)/10$^4$ | 7.5 | 8.5 | 3.5 | 6.3 |

Test 2 provided the results that the hairs treated with the hair cosmetic composition of the present invention were longer in characteristic life according to the treatment time, irrespective of the chemical treatment history.

Examples 2 and 3

The shampoo of each composition shown in Table 4 is prepared according to a manner known per se in the art, and applied to the head hair in a mass ratio to the head hair of 0.1; the head hair is washed with bubbles and allowed to stand for 1 minute, and thereafter rinsed with water and dried.

TABLE 4

|  | Example | |
|---|---|---|
| Component/% by mass | 2 | 3 |
| Peptide (2) | 0.1 | 0.01 |
| Peptide (3) | — | 0.02 |
| Benzyloxyethanol | 0.5 | — |
| Benzyl alcohol | — | 1.0 |
| Glycerin | 1.0 | 1.0 |
| Cetrimonium chloride | 0.5 | 0.5 |
| Sodium laureth sulfate | 15.0 | 15.0 |
| Lauramide DEA | 2.0 | 2.0 |
| Cocamide propylbetaine | 0.5 | 0.5 |
| Polyquaternium-10*[1] | 0.2 | 0.2 |
| Fragrance | 0.5 | 0.5 |
| Propylparaben | 0.5 | 0.5 |
| 90% Lactic acid*[2] | q.s. | q.s. |
| Sodium chloride*[3] | Viscosity control | Viscosity control |
| Purified water | Balance | Balance |
| Total | 100 | 100 |

*[1]Poiz C-80M, product of Kao Corp.
*[2]In an amount to make pH 5.0.
*[3]In an amount to make the viscosity measured with a B-type rotation viscometer (B8R Viscometer, product of TOKIMEC Inc.) equipped with a helical stand be 3,000 mPa · s.

Examples 4 and 5

The conditioner of each composition shown in Table 5 is prepared according to a manner known per se in the art, applied to the head hair, having been washed with a commercially available shampoo, in a mass ratio to the head hair of 0.1 and allowed to stand for 5 minutes; and thereafter the head hair is washed and rinsed with water and dried.

TABLE 5

|  | Examples | |
|---|---|---|
| Component/% by mass | 4 | 5 |
| Peptide (1) | 0.5 | 0.1 |
| Peptide (3) | — | 0.2 |
| Benzyl alcohol | — | 2.0 |
| Benzyloxyethanol | 0.2 | — |
| 1,3-BG | 1.0 | — |
| Glycerin | — | 1.5 |
| Cetrimonium chloride | 1.0 | 1.0 |
| Cetanol | 2.5 | 2.5 |
| PEG/PPG-20/22 butyl ether dimethicone*[4] | 0.5 | 0.5 |
| Hydroxyethyl cellulose*[5] | 0.5 | 0.5 |
| Paraben | 0.5 | 0.5 |
| Fragrance | 0.2 | 0.2 |
| Malic acid*[6] | q.s. | q.s. |
| Purified water | Balance | Balance |
| Total | 100 | 100 |

*[4]KF-6012, product of Shin-Etsu Chemical Co., Ltd.
*[5]SE900, product of Daicel Chemical Industries, Ltd.
*[6]In an amount to make pH 5.0.

Example 6

The treatment agent of the composition shown in Table 6 is prepared according to a manner known per se in the art, applied to the head hair, having been washed and towel dried, in a mass ratio to the head hair of 0.2 and allowed to stand for 10 minutes; and thereafter the head hair is washed and rinsed with water and dried.

TABLE 6

| Component/% by mass | Example 6 |
|---|---|
| Peptide (1) | 0.02 |
| Peptide (2) | 0.02 |
| Benzyl alcohol | 5.0 |
| Stearyl alcohol | 3.1 |
| Isopropyl palmitate | 1.0 |
| Propylene glycol | 3.5 |
| Ethanol | 2.0 |
| Dimethicone*[7] | 0.5 |
| Hydroxyethyl cellulose*[8] | 0.5 |
| Fragrance | 0.5 |
| 90% Lactic acid*[9] | q.s. |
| Purified water | Balance |
| Total | 100 |

*[7]BY11-026, product of Dow Corning Toray Co., Ltd.
*[8]SE900, product of Daicel Chemical Industries, Ltd.
*[9]In an amount to make pH 5.0.

Example 7

The hair dressing of the composition shown in Table 7 is prepared according to a manner known per se in the art, and applied to the head hair, having been washed and towel dried immediately after wake-up, in a mass ratio to the head hair of 0.3 so as to make the hair style; taking a bath is performed before going to bed, to wash away the hair dressing.

TABLE 7

| Component/% by mass | Example 7 |
| --- | --- |
| Peptide (1) | 0.01 |
| Peptide (2) | 0.01 |
| Peptide (3) | 0.01 |
| Benzyl alcohol | 5.0 |
| Ethanol | 6.0 |
| Polyquaternium-11[10] | 4.0 |
| Polysolvate 80[11] | 0.2 |
| Cetyl acetate | 0.15 |
| Lanolin acetate | 0.15 |
| Stearalkonium chloride | 0.1 |
| Isosteareth-10[12] | 0.1 |
| Orange No. 205 | 0.01 |
| Fragrance | 0.1 |
| Purified water | Balance |
| Total | 100 |

[10]Gafquat 734, product of ISP Japan Ltd.
[11]Reodole TW-0120V, product of Kao Corp.
[12]Nonion IS-210, product of NOF Corp.

Example 8

The first and second parts of a bleach of the compositions shown in Table 8 are prepared according to a manner known per se in the art. Immediately before the application, the first part and the second part are mixed together in a ratio of 1:1. The bleach prepared by the mixing is applied to the head hair in a mass ratio to the head hair of 1 and allowed to stand for 20 minutes; and thereafter the head hair is washed with water. Then, the head hair is washed with a commercially available shampoo, and thereafter treated with a commercially available hair conditioner and then dried.

TABLE 8

| | Component/% by mass | Example 8 |
| --- | --- | --- |
| First part | Peptide (1) | 0.02 |
| | 28% by mass Aqueous ammonia | 0.02 |
| | Benzyl alcohol | 5.0 |
| | Ethanol | 15.0 |
| | Propylene glycol | 10.0 |
| | Octyldodeceth-20 | 10.0 |
| | Oleamide DEA | 8.0 |
| | Oleyl alcohol | 2.0 |
| | Ammonium chloride[13] | q.s. |
| | Purified water | Balance |
| | Total | 100 |
| Second part | Cetanol | 2.0 |
| | Sodium lauryl sulfate | 1.0 |
| | Hydrogen peroxide (35% by mass) | 17.0 |
| | Methylparaben | 0.1 |
| | Phosphoric acid[14] | q.s. |
| | Purified water | Balance |
| | Total | 100 |

[13]In an amount to make pH 10.
[14]In an amount to make pH 3.5.

The invention claimed is:

1. A hair cosmetic composition, comprising:
   (a) a peptide which is free of sulfur-containing amino acid residues and which
   (1) consists of 20 or 22 amino acid residues;
   (2) has a molecular weight of 1500 to 3500;
   (3) comprises 4 or 5 basic amino acid residues;
   (4) comprises 10 or 16 non-polar amino acid residues;
   (5) has a C-terminal lysine residue; and
   (6) has a at least 80% homology to an amino acid sequence selected from the group consisting of SEQ ID NO: 1, SEQ ID NO: 2, and SEQ ID NO: 3; and
   (b) 0.1 to 5 mass % of an aromatic alcohol.

2. The hair cosmetic composition according to claim 1, wherein the aromatic alcohol (b) is at least one of benzyl alcohol or benzyloxyethanol.

3. The hair cosmetic composition according to claim 1, wherein the peptide (a) consists of:
   the amino acid sequence of SEQ ID NO: 1.

4. The hair cosmetic composition according to claim 1, wherein the peptide (a) consists of:
   the amino acid sequence of SEQ ID NO: 2.

5. The hair cosmetic composition according to claim 1, wherein the peptide (a) consists of:
   the amino acid sequence of SEQ ID NO: 3.

6. A hair treatment method, comprising applying the hair cosmetic composition according to claim 1 to hair.

7. The hair treatment method according to claim 6, further comprising:
   allowing the hair cosmetic composition to stand in the hair for 1 minute to 24 hours; and
   thereafter washing the hair cosmetic composition from the hair.

* * * * *